United States Patent
Zurlo et al.

(10) Patent No.: US 10,809,247 B2
(45) Date of Patent: Oct. 20, 2020

(54) METHODS FOR EXTRACTING PROTEINS FROM BLOOD PLASMA

(71) Applicant: Plasma Technologies, LLC, Kiawah Island, SC (US)

(72) Inventors: Eugene Zurlo, Charleston, SC (US); Dennis Curtin, Plattsburgh, NY (US)

(73) Assignee: Plasma Technologies, LLC, Charleston, SC (US)

( * ) Notice: Subject to any disclaimer, the term of this patent is extended or adjusted under 35 U.S.C. 154(b) by 0 days.

(21) Appl. No.: 15/767,639

(22) PCT Filed: Oct. 14, 2016

(86) PCT No.: PCT/US2016/057196
§ 371 (c)(1),
(2) Date: Apr. 11, 2018

(87) PCT Pub. No.: WO2017/066683
PCT Pub. Date: Apr. 20, 2017

(65) Prior Publication Data
US 2018/0306772 A1    Oct. 25, 2018

Related U.S. Application Data

(60) Provisional application No. 62/242,165, filed on Oct. 15, 2015.

(51) Int. Cl.
*G01N 33/49* (2006.01)
*C07K 1/18* (2006.01)
(Continued)

(52) U.S. Cl.
CPC ......... *G01N 33/491* (2013.01); *B01D 15/12* (2013.01); *B01D 15/3804* (2013.01); *C07K 1/18* (2013.01);
(Continued)

(58) Field of Classification Search
CPC ...... G01N 33/491; G01N 30/04; G01N 30/06; G01N 2030/062; G01N 2030/065;
(Continued)

(56) References Cited

U.S. PATENT DOCUMENTS 4,639,513 A * 1/1987 Hou ............... B01J 20/3217
424/177.1
6,835,379 B2 * 12/2004 Andersson ........... C07K 16/065
424/130.1
(Continued)

FOREIGN PATENT DOCUMENTS

WO    20070030244 A2    3/2007

OTHER PUBLICATIONS

Extended European Search Report for European Patent Application No. 16856348A - 1109, dated Oct. 4, 2018, 8 pages.

*Primary Examiner* — Katherine Zalasky McDonald
(74) *Attorney, Agent, or Firm* — Fish IP Law, LLP

(57) ABSTRACT

A method of producing protein products including alpha-1-proteinase inhibitor, gamma globulin, albumin, and other proteins from plasma includes steps of: (1) adding a salt to the blood product to produce a first intermediate, wherein the salt comprises between 11-13 wt % of the first intermediate; (2) separating the first intermediate to produce a first supernatant and a first paste; (3) adding a salt to the first intermediate to produce a second intermediate, wherein the salt comprises between 21-23 wt % of the second intermediate; (4) separating the second intermediate to produce a second supernatant and a second paste; (5) separating a third intermediate from the second supernatant by affinity chromatography; and (6) separating the third intermediate by ion exchange chromatography to produce an eluate containing the protein product. Advantageously, the inventive methods (Continued)

are simple and produce alpha-1-proteinase inhibitor, gamma globulin, albumin, and other proteins in high yields.

22 Claims, 2 Drawing Sheets

(51) Int. Cl.
*C07K 1/22* (2006.01)
*C07K 1/32* (2006.01)
*C07K 14/81* (2006.01)
*B01D 15/12* (2006.01)
*B01D 15/38* (2006.01)
*G01N 30/02* (2006.01)
*G01N 30/88* (2006.01)

(52) U.S. Cl.
CPC ............... *C07K 1/22* (2013.01); *C07K 1/32* (2013.01); *C07K 14/81* (2013.01); *C07K 14/8125* (2013.01); *G01N 30/02* (2013.01); *G01N 2030/8822* (2013.01)

(58) Field of Classification Search
CPC ........ G01N 2030/14; G01N 1/28; G01N 1/40; G01N 1/4055; G01N 1/34; G01N 2001/4061; G01N 2001/4066; G01N 2001/4088; G01N 2001/4083; B01D 15/38; B01D 15/3804; B01D 15/3809; B01D 15/3823; B01D 15/12; B01D 15/125; B01D 11/04; B01D 11/0492; C07K 1/18; C07K 1/122; C07K 1/32; C07K 1/303; C07K 1/30; C07K 1/34; C07K 1/36; C07K 14/8125; C07K 14/8128; C07K 16/00

See application file for complete search history.

(56) References Cited

U.S. PATENT DOCUMENTS

| | | | |
|---|---|---|---|
| 7,297,716 B2 | 11/2007 | Shanbrom | |
| 7,879,331 B2 | 2/2011 | Zurlo et al. | |
| 7,879,332 B2 | 2/2011 | Zurlo et al. | |
| 8,293,242 B2 | 10/2012 | Zurlo et al. | |
| 2007/0049732 A1* | 3/2007 | Zurlo | C07K 14/765 530/387.1 |
| 2007/0049734 A1* | 3/2007 | Zurlo | A61M 1/3693 530/387.1 |
| 2011/0152503 A1* | 6/2011 | Zurlo | A61K 38/57 530/369 |
| 2019/0055282 A1* | 2/2019 | Zurlo | C07K 14/81 |

* cited by examiner

METHODS FOR EXTRACTING PROTEINS FROM BLOOD PLASMA

FIELD OF THE INVENTION

The field of the invention is improved methods for increasing the purity and yields of alpha-1-proteinase inhibitor (also known as alpha-1 antitrypsin) or other protein products.

BACKGROUND

The following background discussion includes information that may be useful in understanding the present invention. It is not an admission that any of the information provided herein is prior art or relevant to the presently claimed invention, or that any publication specifically or implicitly referenced is prior art.

U.S. Pat. No. 7,297,716 to Shanbrom discloses methods of isolating blood products (e.g., fibrin glue) from cryoprecipitate. Shanbrom's methods use salts to increase the yield of cryoprecipitate. For example, 2-10 wt % sodium citrate is added to blood or plasma. Sodium citrate at this concentration inactivates and/or inhibits pathogenic microorganisms, prevents cells and proteins from denaturing, increases the yield of cryoprecipitate (even without freezing), and facilitates the removal of denatured components. From the cryoprecipitate, Shanbrom contemplates isolation of various clotting factors including fibrinogen, factor II, factor V, factor VII, factor VIII, factor IX, factor X, and platelets. However, Shanbrom fails to appreciate that salts can be added to previously frozen blood products to concentrations above 11 wt %. Moreover, Shanbrom further fails to appreciate that protein products can be extracted from any supernatant, including the supernatants formed from intermediates having 11-13 wt % and 21-23 wt % salt.

One protein product is alpha-1-proteinase inhibitor ("A1PI"). A1PI is a 52 kDa glycoprotein in the serpin superfamily of protease inhibitors. Normally, A1PI protects tissues, such as the elastic tissues of the lungs, from neutrophil elastase, especially at inflammation sites. A genetic deficiency of A1PI can lead to emphysema, chronic obstructive pulmonary disease, and cirrhosis. A1PI can be administered to prevent damage that would be caused if A1PI deficiencies were left untreated.

U.S. Pat. No. 4,697,003 to Coan discloses a method for separating A1PI from aqueous solutions of plasma proteins. Coan's method builds on the Cohn ethanol fractionation technique, which involves thawing fresh frozen plasma, removing the precipitate, and ethanol is added in five stages to a concentration of about 40%. The first step of Coan's method is to desalt Cohn Effluent II+III, Effluent I, or cryosupernatant. Next, the desalted solution is contacted with an anion exchange resin, and the A1PI selectively binds to the resin. An eluant displaces the A1PI into an eluate. Finally, A1PI is recovered from the eluate. However, ethanol and other alcohols can be problematic because they tend to denature the desirable proteins, such as A1PI.

U.S. Pat. No. 8,580,931 to Kumpalume et al. also describes methods of isolating A1PI that include subjecting A+1 supernatant to two metal chelate chromatography steps. Borrowing terminology from the Kistler Nitschmann process, A+1 supernatant is the combination of precipitate A and fraction 1. However, the preparation of the A+1 supernatant also involves adding 17-21% (v/v) ethanol, which can denature desirable proteins as noted above. See also, DE3874376 to Thierry.

In U.S. Pat. Nos. 7,879,331; 7,879,332; and 8,293,242, the inventors conceived of a salting procedure that eliminates the use of ethanol in extracting protein products from blood products.

In the current inventive subject matter, the inventors discovered simplified methods in which cryoprecipitate need not be separated from the cryoprecipitate poor plasma before the salt precipitation steps. Additionally, in cases when very little protein product remains in the first and second pastes, high yields of protein product can be maintained without re-dissolving the pastes and conducting further purification steps. In the case of A1PI, the inventors discovered that very little A1PI precipitates at a salt concentration of 22 wt %. This result is surprising in view of literature that teaches A1PI precipitates at high salt concentrations. Because very little A1PI is lost in pastes, high yields can be obtained from the second supernatant. Thus, the processes are improved by elimination of the paste processing.

The second supernatant can be applied to an affinity column with minimal pre-processing (e.g., bioburden filtration, solvent/detergent treatment, diafiltration), further simplifying the isolation of protein products. On the other hand, it is contemplated to incorporate an endotoxin removal step, either upstream or downstream of the affinity column. Contemplated endotoxin removal steps include treatment with polymyxin B or other affinity media (e.g., resins or membranes).

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

SUMMARY OF THE INVENTION

The inventive subject matter provides methods in which one can produce a protein product from a blood product that includes plasma. Preferred methods include steps of (1) adding a salt to the blood product to produce a first intermediate, wherein the salt comprises between 11-20 wt % of the first intermediate; (2) separating the first intermediate to produce a first supernatant and a first paste; (3) adding a salt to the first supernatant to produce a second intermediate, wherein the salt comprises between 15-30 wt % of the second intermediate; (4) separating the second intermediate to produce a second supernatant and a second paste; (5) separating a third intermediate from the second supernatant by affinity chromatography; and (6) separating the third intermediate by ion exchange chromatography to produce an eluate containing the protein product.

In regard to the blood product that includes plasma, the inventors contemplate that any of Source Plasma, fresh frozen plasma, Recovered Plasma, or salvaged plasma can be used in methods consistent with the inventive subject matter. It should be appreciated that although the methods described herein do not necessarily require a frozen plasma containing product as a starting material, conventional plasma containing products are typically frozen, and a thawing step is usually required before further processing or purification.

With respect to the salt added to the blood product, there is a wide range of salts that can be used, including for example (without limitation), citrates, acetates, and/or gluconates. Suitable salts are water-soluble. Although use of water-soluble salts is preferred, use of water-insoluble salts (e.g., calcium citrate or other salts with low solubility in water) with chelating agents (e.g., EDTA) that improve the solubility of insoluble salts is not excluded. Typically a first precipitate and a first supernatant form in first intermediates having salt contents of between 10.1-25 wt %, more typically, 10.1-11, 11-13, 13-15, and 15-20 wt %. Protein separation can sometimes be improved by pH adjustment to a specific value in the range from 3 to 10 and/or by adjusting the temperature of the mixture to a specific value in the range from 0 to 25° C.

It should be appreciated that the step of separating the first intermediate to produce a first supernatant and a first paste can be achieved by centrifugation or filtration. When centrifugation is used, the first precipitate forms a pellet (i.e., the first paste) from which the first supernatant can be decanted, pipetted, or otherwise removed. At larger process scales, filtration is preferable to centrifugation. When filtration is used, the first supernatant is the filtrate and the first precipitate forms the filter cake (i.e., the first paste).

In regard to the second supernatant, typical salt contents of between 15 and 30 wt % more typically 15-21, 21-23, 23-25, 25-27, and 27-30 wt % are contemplated. Because salt is added to the first supernatant, the salt content of the second intermediate will be greater than the salt content of the first intermediate. Protein separation might be improved by pH adjustment to a specific value in the range from 3 to 10 and/or by adjusting the temperature of the mixture to a specific value in the range from 0 to 25° C. The same considerations applied to the separation of the first supernatant and the first precipitate can be applied to the separation of the second supernatant from the second precipitate.

In an exemplary embodiment of the inventive methods, prior to subjecting the second supernatant to affinity chromatography, the second supernatant can be filtered to remove bioburden, treated with a solvent and a detergent to inactivate any enveloped viruses in the second supernatant, and/or desalted (e.g., by diafiltration and/or ultrafiltration). As used herein, diafiltration means filtration used to exchange the solution/buffer containing the protein product. Ultrafiltration, as used herein is a filtration process that concentrates a solution of the protein product. For diafiltration and ultrafiltration, both perpendicular and tangential flow configurations are contemplated. Advantageously, diafiltration and/or ultrafiltration remove both salt and low molecular weight species.

In another exemplary embodiment, an appropriate affinity resin is used in the step of separating a third intermediate from the second supernatant by affinity chromatography. Affinity resins can be purchased from suppliers such as Bio-Rad, Sigma-Aldrich, GE Healthcare Life Sciences, Thermo Fisher Scientific, Merck Millipore, GenScript, and ProMetic Life Sciences.

In production of A1PI, for example, an A1PI specific affinity resin is used to produce a third intermediate that contains A1PI. Similarly, an albumin-specific affinity resin can be used to isolate albumin from the second supernatant. Therefore, it should be apparent that the second supernatant can be applied to numerous affinity chromatography columns in series to extract different proteins. For example, the affinity chromatography step in the production of A1PI produces a flow-through and a wash. The flow-through and/or wash can be applied to an albumin-specific affinity column. The flow-through and/or wash from the albumin specific affinity column can then be applied to a third affinity column specific to the same or a different protein.

To remove other viruses from the protein product, the eluate can be sterile filtered. Methods according to the inventive subject matter are especially suitable for the preparation of protein products including A1PI, gamma globulin, albumin, and/or other proteins.

In other aspects, the inventive methods may further comprise isolating a second protein product from the first paste or the second paste. Additionally, a second protein product may be isolated from a flow-through and/or a wash produced in the course of the affinity chromatography step. Therefore, it should be apparent that the second protein product can be different from the first protein product, and may comprise A1PI, gamma globulin, albumin, and/or other proteins.

In yet further aspects of the inventive subject matter, methods of producing gamma globulin may further comprise isolating gamma globulin from the second paste.

Various objects, features, aspects and advantages of the inventive subject matter will become more apparent from the following detailed description of preferred embodiments, along with the accompanying drawing figures in which like numerals represent like components.

DETAILED DESCRIPTION

The inventive subject matter provides improved methods of producing protein products in high yields from a blood plasma containing product. Blood plasma contains numerous proteins and clotting factors that are useful therapeutics. For example, A1PI is used to treat people with A1PI deficiency, which can cause a breakdown in lung tissue. Another class of plasma proteins is gamma globulins, which are used to treat immune deficiencies and disorders. Albumin and other proteins (e.g., fibrinogen, prothrombin, alpha-1-acid glycoprotein, alpha-1-fetoprotein, alpha-2-macroblobulin, beta-2-microglobulin, haptoglobin, ceruloplasmin, complement component 3, complement component 4, C-reactive protein, transferring, mannose-binding lectin etc.) can also be isolated from plasma by methods according to the inventive subject matter.

In preferred embodiments, the blood plasma containing product comprises Recovered Plasma or salvaged plasma, and more preferably fresh frozen plasma, and even more preferably Source Plasma. It should be appreciated that blood plasma containing products are typically stored and transported in a frozen state, and are thawed before further processing or purification. In the thawing process, the plasma may separate into a cryoprecipitate and a cryoprecipitate-poor plasma ("cryo-poor" plasma). As used herein "cryo-poor" plasma refers to the liquid supernatant that results from thawing frozen plasma, and which does not include the cryoprecipitate. Preferably the whole plasma, i.e., both the cryo-poor plasma and the cryoprecipitate, is carried through further processing steps, although use of only the cryo-poor plasma in subsequent processing steps is not excluded. Optionally, the cryoprecipitate can be reincorporated (e.g., by mixing) in the cryo-poor plasma prior to or as part of protein product production.

Example 1. Preparation of Human Plasma for Fractionation

An exemplary blood plasma containing product was prepared by allowing frozen human plasma (7 L; 28 0.25 L bags) to thaw at 2-8° C. for 24-48 hours in a refrigerator. The bags were sprayed with sterile alcohol, then the top of each bag was cut and the contents poured into a clean, tared vessel. The total weight of the vessel was recorded. An overhead stirrer was mounted over the vessel and the plasma was stirred for 60 minutes at 312 rpm at 20° C. A sample of the plasma was taken to determine its weight and density. The resulting blood plasma containing product was used in the preparation of the first intermediate as described in Example 3, below.

Figure 1:
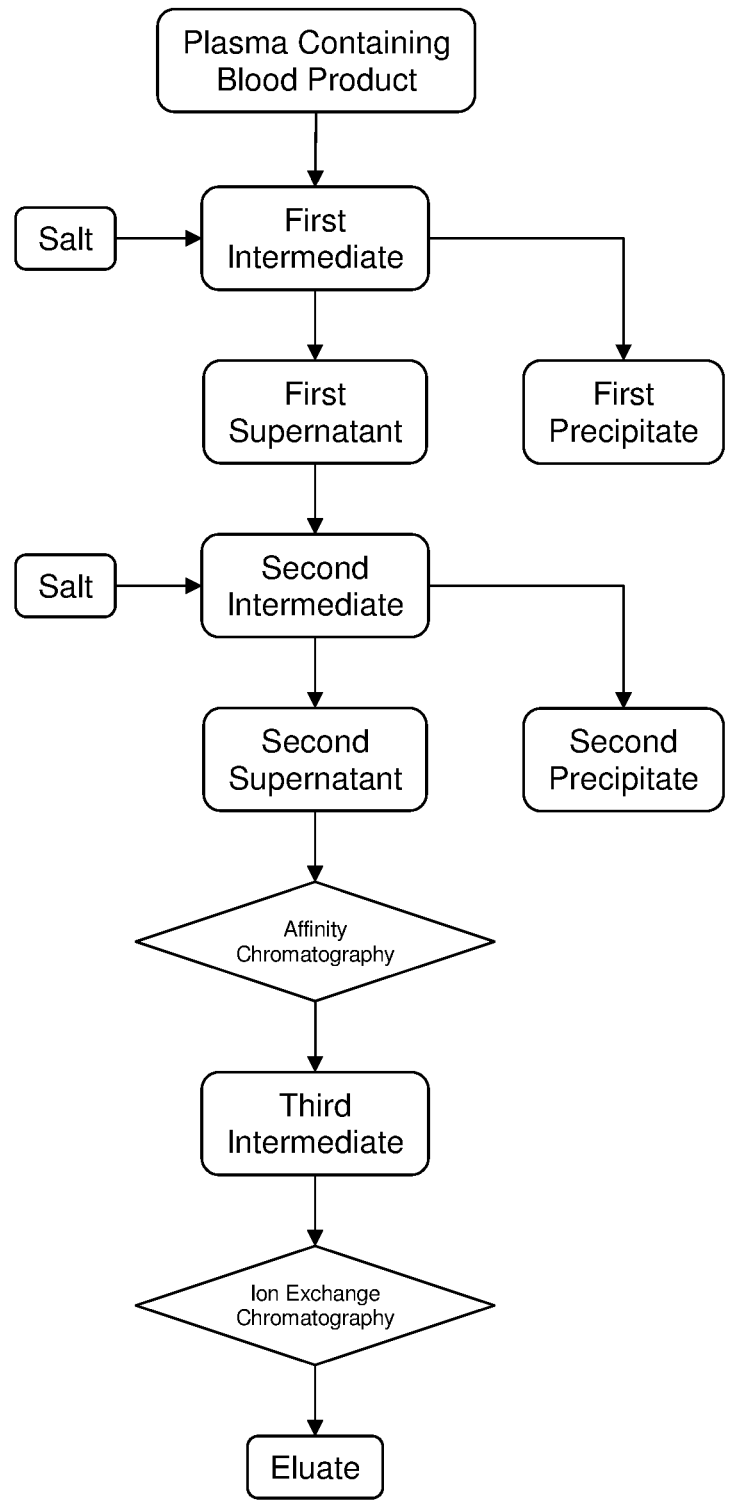
FIG. 1 is a schematic of a method of producing a protein product from a blood product.

In FIG. 1 a flow diagram of one embodiment of the inventive subject matter is shown. A fresh or thawed blood plasma containing product and a salt are mixed, forming the first intermediate that is typically 10-25 wt % added salt, more typically 10-11, 11-13, 13-15, and 15-20 wt % added salt, preferably, 11-13 wt %, and more preferably 12 wt % the added salt. Suitable salts for use in the inventive methods include, but are not limited to citrates, acetates, and gluconates. Although solid salt can be added to the blood plasma product, in preferred methods salt solutions are added to the blood plasma product. Depending on the desired protein product, the pH of the salt solutions can be adjusted from about pH 3 to pH 8 to optimize protein fractionation.

Example 2. Preparation of a 50% Citrate Stock Solution

A 50% citric acid solution was prepared by dissolving 500 g of citric acid in 600 mL of purified water, e.g., water for injection ("WFI"), stirring for 30-60 minutes until dissolved. The solution volume was adjusted to 1000 mL by addition of purified water. A 50% sodium citrate solution was prepared by adding 500 g of trisodium citrate into 600 mL of stirred purified water and stirring for 30-60 minutes until dissolved. While measuring the pH of the sodium citrate solution, the citric acid solution was slowly added to the stirred sodium citrate solution until a pH of 7.0±0.02 was obtained. Purified water was added with stirring to the pH-adjusted sodium citrate solution to dilute the solution to 1000 mL. This solution is referenced below as FS.

The plasma, intermediates, and supernatants can be processed at temperatures between the freezing point of the solution and ambient temperature, generally between 0 and 25° C. In one embodiment, the blood plasma product is maintained at 20° C. and room temperature citric acid/citrate solution (e.g., FS) is added to the plasma until the citric acid/citrate comprises 11-13 wt %, and preferably 12 wt % of the first intermediate so obtained. The addition of the salt will cause the first intermediate to separate into a first precipitate and a first supernatant. In another embodiment, the first intermediate is stirred and cooled to between 2-8° C. generating a precipitate. The first precipitate contains high molecular weight proteins and most lipids. Preferably, the first intermediate is stirred until precipitation is complete (typically for 60 minutes or more).

Example 3. Production of the First Intermediate: Citrate Precipitation (12%) of Human Blood Plasma Containing Product The vessel and the blood plasma containing product from Example 1 were cooled to 4±3° C. The amount of FS from Example 2 to be added was calculated using the formula: volume (mL) of $FS=315.8 \times w/d$, where w=total plasma weight (corrected for sample removed in Example 1) and d is the sample density from Example 1. The required volume of FS was dispensed and added slowly to the chilled, gently stirred, pooled plasma over 5-10 minutes, producing the first intermediate. The stirrer was removed and the weight of the vessel and its contents was recorded. The vessel contents were stirred for 60 minutes maintaining a temperature of the vessel contents of 2-8° C. The first supernatant and the first precipitate can be separated into the first supernatant and the first paste by centrifugation or filtration as described above.

Example 4. Separation of the First Intermediate

Pre-chilled centrifuge bottles were tared and filled with the vessel content until all vessel content had been transferred. Each chilled centrifuge bottle was centrifuged at 4200 rpm for 60 minutes. The first supernatant was gently poured from each centrifuge bottle into a clean tared 10 L bottle. This was repeated until each centrifuge bottle was processed. The weight of each centrifuge bottle was determined to enable calculation of the total weight of the residual material, the first paste(s) ("Paste1"). Paste1 was transferred from each bottle to a 5 L bottle. Each centrifuge bottle was rinsed with 50 mM Tris-HCl pH 7.40 buffer, using 1 L of buffer in total. Paste 1 was retained for possible further processing. A small sample of supernatant was taken to determine its density. The weight of first supernatant ("Super1") was determined by weighing the 10 L bottle and calculating the weight of Super 1.

In an exemplary embodiment, the first supernatant is cooled to 2-8° C., and additional citric acid/citrate solution is added to the first supernatant producing the second intermediate, which comprises 15-21, 21-23, 23-25, 25-27, and 27-30 wt % citric acid/citrate, preferably 21-23 wt % citric acid/citrate, and more preferably 22 wt % citric acid/citrate. Use of salt/buffer combinations other than citric acid/citrate is also contemplated. One having ordinary skill in the art appreciates that the concentration of salt in the second intermediate is greater than the concentration of salt in the first intermediate. Preferably, the second intermediate is stirred until formation of the second precipitate is complete, for example, overnight. Immune globulins can be found in the second precipitate.

Example 5. Production of the Second Intermediate: Citrate Precipitation (22%) of Super1

The 10 L bottle containing Super1 from Example 4 was cooled so that contents were in the temperature range of 2-8° C. The amount of FS (from Example 2) was calculated using the formula: volume of FS (mL)=$410 \times w/d$, where w=weight of the supernatant and d is its density; both from Example 4. The calculated quantity of FS was added to gently-stirred chilled Super1, producing the second intermediate. The resulting second intermediate was incubated for at least one hour, maintaining a temperature of the vessel contents of 2-8° C.

Like the first intermediate, the second intermediate can be separated into a second supernatant and a second paste by centrifugation and/or filtration. When centrifugation is used, the second paste is the pellet formed from the second precipitate, and the second supernatant can be decanted, pipetted, or otherwise removed from the pellet. When filtration is used, the second paste is the filter cake formed by the second precipitate, and the second supernatant is the filtrate.

Example 6. Separation of the Second Intermediate

Pre-chilled centrifuge bottles were tared and each was filled with the second intermediate until all the second intermediate had been transferred. Each chilled centrifuge bottle was centrifuged at 4200 rpm for 60 minutes. The second supernatant was gently poured from each centrifuge bottle into a clean tared 10 L bottle. This was repeated until each centrifuge bottle was processed. The weight of each centrifuge bottle was measured to determine the total weight of the residual material, the second paste(s) ("Paste2"). Paste2 was transferred from each bottle to a 5 L bottle. Each centrifuge bottle was rinsed with 50 mM Tris-HCl 0.15M NaCl pH 7.40 buffer, using 2 L of buffer in total. Paste2 was retained for possible further processing. A small sample of the second supernatant was removed to determine its density. The weight of the second supernatant was calculated by weighing the 10 L bottle and calculating the weight of the second supernatant ("Super2").

Figure 2:
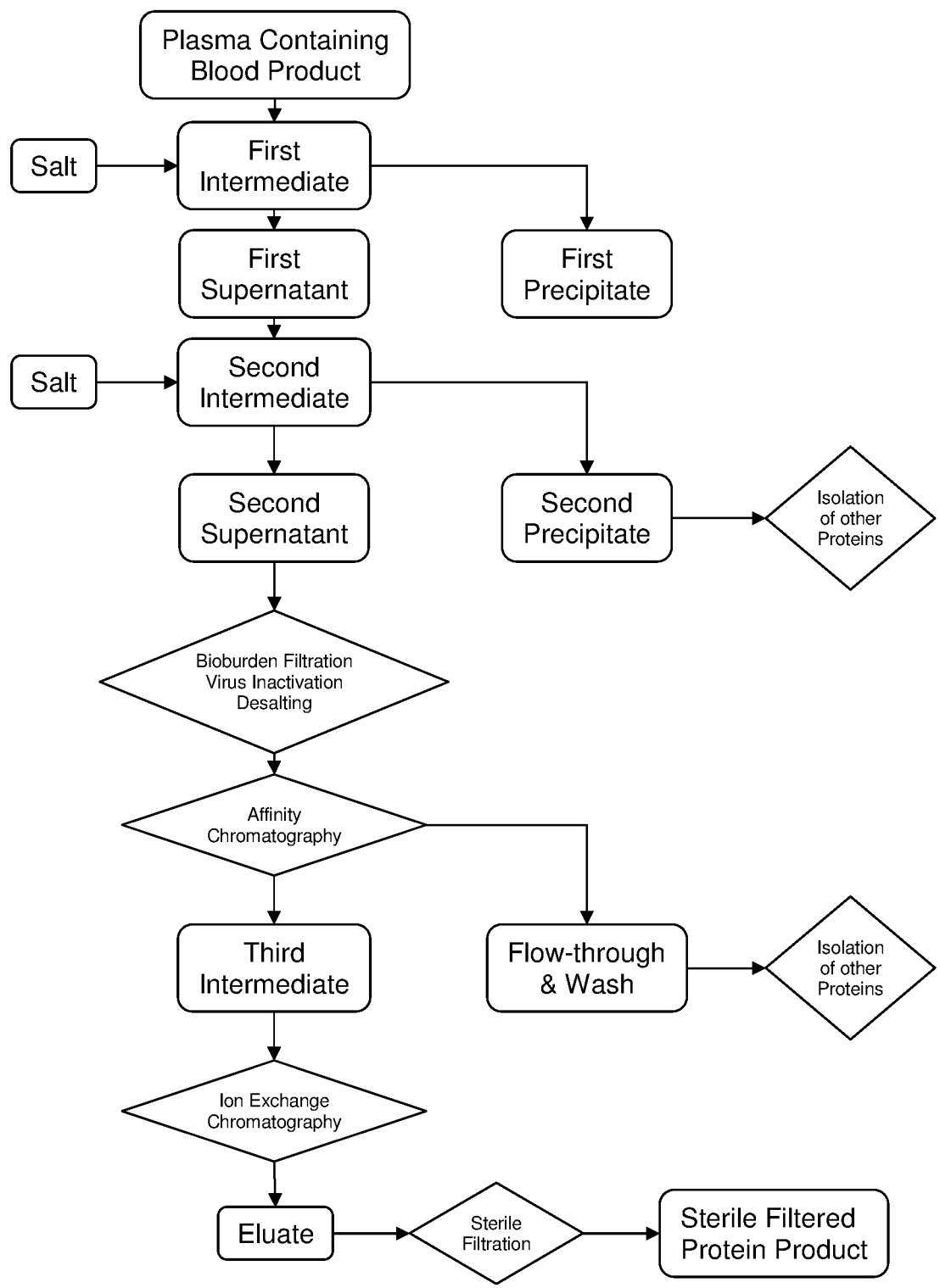
FIG. 2 is a schematic of another method of producing a protein product from a blood product.

Optionally, as shown in FIG. 2, the second supernatant can be filtered to remove bacteria, fungal spores, hyphae, and other "bioburden" using bioburden reduction filters. Exemplary bioburden reduction filters include filters made under the Sartorius, Pall, and EMD Millipore brands (e.g., Sartopore 2XLG 0.8/0.2, Supra EK1P/EAV1.5/0.2, Milligard®, Polysep® II, Lifegard™, Clarigard®, Polygard®-CN, Polygard®-CR, Polygard®-CT, etc.).

Example 7. Bioburden Reduction

Super2, from Example 6, was filtered through a 0.021 m² filter surface area Sartopore 2 XLG 0.2 µm pore size filter. A pump was employed, ensuring that pressure did not exceed 15 psi across the filter. The filtrate was collected in a tared 20 L Hyclone bag. The weight of filtrate was recorded.

Another optional step is to reduce the citrate concentration by diafiltration/ultrafiltration. The size of the filter can be selected to maximize flow rate (e.g., 3-6 L/h) while preventing the protein of interest from flowing through the filter with the filtrate. For example 30 kD membranes retain A1PI but allow relatively fast flow of the liquid through the membrane. Reduction in citrate concentration can be correlated with a reduction in conductivity from about 55-60 mS/cm to about 10 mS/cm, and most preferably to 5 mS/cm or less.

Example 8. First UF/DF Treatment

UF/DF treatment of filtrate from Example 7 was employed to reduce volume and remove low molecular weight solutes. Sartorius cassettes (PESU-30 kDa; 0.1 m² membrane surface area) were used. The UF/DF system was assembled and the hold-up volume of the system recorded. A feed volume/membrane area of approximately 32 and flow rate of 24 mL/min were employed. Diafiltration using WFI (conductivity below 10 mS/cm) was performed maintaining an inlet pressure of 15-20 psi and retentate pressure of 0-5 psi. Diafiltration was continued until the target conductivity of retentate was achieved, then the retentate was concentrated to 1 hold-up volume. The UF/DF system was flushed with 1 hold-up volume of WFI. Retentate and wash were combined ("Retentate1"). The weight of the diafiltered pool was determined, and a sample was removed to determine the concentration of A1PI by nephelometry.

Inactivation of enveloped viruses can be achieved by denaturing the viral envelope membrane lipids. For example, a solvent/detergent (e.g., tri-n-butyl phosphate and polysorbate 80; tri-n-butyl phosphate and Triton™ X-100, or tri-n-butyl phosphate and detergent) can be used to treat the second supernatant. Advantageously, solvent/detergent treatment may also kill bacterial and fungal contamination and wash away endotoxins. In a preferred embodiment of the inventive subject matter, 13.2 g of a 23.09:76.91 mixture of tri-n-butyl phosphate and polysorbate 80 per kg of the second supernatant is added to the second supernatant.

Example 9. Solvent Detergent Treatment

The bioburden reduced Retentate1 from Example 8 was virally inactivated by solvent detergent treatment. A solvent detergent stock solution of 10% Tween® 80 and 3% tri-n-butyl phosphate was produced using WFI. The amount (g) of solvent detergent stock solution to be used was calculated by multiplying the weight of Retentate1 (kg) by 13.2. The calculated amount of solvent detergent stock solution was gradually added to the Retentate1. The solution was incubated for 6 to 10 hours at 22 to 29° C.

The inventors contemplated that affinity resins could be used to isolate individual components of protein products. For example, ProMetic BioSciences Ltd. and ProMetic BioTherapeutics produce affinity resins that specifically bind coagulating factors, plasminogen, fibrinogen, immune globulins, albumin, A1PI. GE Healthcare produces a cross-linked agarose resin bearing a single-domain antibody that binds A1PI. The amount of resin required depends on the amount of protein in the second supernatant and the loading capacity of the resin. Typically after application of the second supernatant, the affinity resin is washed with a salt solution (e.g., 100 mM NaCl) that removes proteins adsorbed to the resin by non-specific electrostatic interactions. The desired protein is then eluted from the affinity column using an eluate recommended by the resin manufacturer, although use of other elution protocols are not excluded. In the case of A1PI and the GE Healthcare resin, the protein product can be eluted from the affinity chromatography column using a buffered magnesium chloride solution (e.g., 2 M $MgCl_2$ in 50 mM Tris-HCl, pH 7.40). Typical protein product yields after the affinity chromatography step range between 70% and 98%.

Example 10. A1PI Affinity Chromatography

The solvent detergent-treated Retentate1 from Example 9 was subjected to A1PI affinity chromatography. GE Alpha-1 Antitrypsin Select resin was used and prepared according to manufacturer's instructions. The resin was packed into a GE HiScale 50/40 column with ~30 cm bed height (~590 mL column volume). The entire volume of Retentate1 from Example 9 was loaded onto the column and an operational flow rate of 167 cm/h was used for this purification step. The column was equilibrated at this flow rate using 50 mM Tris-HCl buffer at pH 7.4 until a stable conductivity and $A_{280}$ baseline of the eluate were achieved (about three column volumes). Retentate1 from Example 9 was loaded using a sample pump at a flow rate of 42 cm/h. Flow-through was collected during the loading operation. After completion of loading, elution with 50 mM Tris-HCl buffer at pH 7.4 at 167 cm/h was continued until the eluate displayed an A280 at baseline. A step gradient was then initiated to 15% 1 M NaCl/Tris-HCl buffer at pH 7.4 and 85% 50 mM Tris-HCl buffer at pH 7.4. The salt wash peak eluted by this gradient step was collected until the $A_{280}$ returned to baseline. The mobile phase was stepped back to 100% Tris.HCl buffer at pH 7.4, and the column washing with Tris.HCl buffer was continued until the until the A280 peak returned to baseline conductivity returned to baseline. Once conductivity had returned to baseline, flow was switched to an elution buffer consisting of 2M $MgCl_2$, 50 mM Tris-HCl buffer, pH 7.4. The eluate, the third intermediate, was collected from the start of the $A_{280}$ peak until the $A_{280}$ peak returned to baseline. The volume of the third intermediate was recorded and mobile phase was switched 50 mM Tris.HCl buffer, pH 7.4. Column cleaning-in-place (CIP) was subsequently performed by eluting with 3 column volumes of 100 mM thioglycerol solution.

Samples of each wash and the third intermediate were taken, and the concentration of A1PI in each was determined by nephelometry.

Example 11. Thiol Reduction Using Dithiothreitol

The third intermediate was treated with dithiothreitol (DTT) to reduce A1PI dimers to monomers. Sufficient DTT was weighed to be a 5 molar excess to the calculated A1PI in the $MgCl_2$ column eluate. Solid DTT was added to the stirred eluate (gentle vortex) at 20-25° C., and stirring was continued for 1 hour. The solution was held overnight at 2-8° C. prior to further processing.

The third intermediate is typically subjected to diafiltration/ultrafiltration to reduce the salt concentration. After diafiltration/ultrafiltration, the conductivity decreases from about 120 mS/cm to less than 10 mS/cm, and preferably 5 mS/cm or less.

Example 12. Second UF/DF Treatment

The third intermediate from Example 11 was subjected to UF/DF treatment to reduce volume and remove low molecular weight solutes. The filter used was a 0.1 $m^2$ membrane surface area Sartorius cassette (PESU-30 kDa). The operation flow rate was 900 mL/min. Two diafiltration buffers were used; 50 mM Tris.HCl buffer, pH 7.4 and a solution of cysteine in Tris.HCl buffer, pH 7.4. The latter solution was prepared by dissolving 50 g cysteine in 10 L of 50 mM Tris, pH 7.4. After assembly of the UF/DF system, the initial conductivity of the solution from example 9 was recorded. Diafiltration was initiated using two diafiltration volumes of the Tris-HCl buffer, then with the cysteine-containing Tris-HCl buffer at constant volume until a conductivity of less than 10 mS/cm was observed. The retentate was collected and the UF/DF system was flushed with the cysteine-containing Tris-HCl buffer. Retentate and wash were combined ("Retentate2").

The inventors expect that any affinity ligand that leaches from the resin into the third intermediate can be separated from the protein product after an ion exchange chromatography step. Suitable resins are supplied by Bio-Rad, Sigma-Aldrich, and Asahi Chemical & Industrial Co. Ltd. (e.g., Asahi Q500 anion exchange resin has exhibited a dynamic binding capacity of 26.5 mg of A1PI per milliliter of resin). In contemplated methods, a 500 ml column of Q500 resin is equilibrated in 50 mM Tris.HCl, pH 7.40. The third intermediate is loaded on the column and eluted with a step gradient from 0 mM to 350 mM NaCl in 50 mM Tris-HCl, pH 7.40 buffer. Where the starting plasma containing blood product is about ten liters, the volume of eluate can yield about one liter.

Example 13. Anion Exchange Chromatography

Final purification of A1PI was performed using anion exchange chromatography of the Retentate2 from Example 12. Cellufine Q500 resin was used, employing a bed height of 25 cm in a GE HiScale 50/40 column (nominal 500 mL bed volume). The column was conditioned by passing 3 column volumes of 2 M NaCl solution at 240 cm/h followed by 3 column volumes of WFI at 240 cm/h. The column was then equilibrated using at least 3 column volumes of 50 mM Tris-HCl, pH 7.4 buffer, until a stable A280 and conductivity baseline were achieved. At this point, Retentate2 from Example 12 was loaded onto the column. The retentate feed bottle was rinsed with 100 mL of 50 mM Tris-HCl buffer, pH 7.4, and the rinse also loaded onto the column. The flow-through during loading was collected. The mobile phase was switched to 50 mM Tris.HCl buffer, pH 7.4, and column washing was continued until a stable $A_{280}$ baseline was obtained. A step gradient was then initiated to 35% 1 M NaCl, 50 mM Tris-HCl buffer, pH 7.4/65% 50 mM Tris-HCl buffer, pH 7.4. Collection of the salt peak was initiated when A280 started to increase, and stopped when the $A_{280}$ peak returned to a stable baseline. A step gradient to 100% 1 M NaCl, 50 mM Tris-HCl buffer, pH 7.4 was then initiated and samples collected. The eluate resulting from the step gradient to 35% 1 M NaCl/65% Tris-HCl buffer contained all of the A1PI. The step gradient to 100% 1 M NaCl removed other impurities.

The inventive methods can further comprise a step of sterile filtration which removes small non-enveloped viruses (e.g., Adenovirus, Parvovirus, papovaviruses, Human papillomaviruses) using a 20 nm pore filter. The sterile filtered protein product can then be further processed depending on the desired formulation. Further processing steps include one or more of ultrafiltration/diafiltration, formulation, a sterile filtration, filling, and lyophilization.

Example 14 Post Viral Filtration

A Planova 75NZ pre-filter and Planova 20N filter were prepared by washing each with 30 mL 50 mM Tris.HCl buffer pH 7.4. The eluate containing A1PI from Example 13 was passed sequentially through the prefilter, then the 20N filter.

Example 15 Third UF/DF Treatment

The filtrate from Example 14 was subjected to UF/DF treatment to reduce volume and remove low molecular weight solutes. The filter used was a Hydrosart cassette (Sartocon slice 20) with 0.018 $m^2$ membrane surface area. Operation flow rate was 54 mL/min. The diafiltration buffer was 20 mM Tris.HCl buffer, 150 mM NaCl pH 7.4. After assembly of the UF/DF system, the system was sanitized with 1 M NaOH at a flow rate of 54 mL/min for 20-30 minutes. Diafiltration with the 20 mM Tris-HCl buffer, 150 mM NaCl, pH 7.4 buffer was initiated and continued until a conductivity of 15 mS/cm was obtained. After calculating the volume needed to achieve an A1PI concentration of 55 mg/mL, the retentate pool was concentrated by ultrafiltration until the A1PI concentration was 55±3 mg/mL by nephelometry. The retentate pool was then over concentrated to 1 holdup volume and retentate was removed and collected. The UF/DF system was flushed with 1 holdup volume of 20 mM Tris.HCl buffer, 150 mM NaCl pH 7.4. The retentate and wash were combined ("Retentate3").

Example 16 Sterile Filtration

Retentate3 was filtered through a 0.22 µm Millex GE PES sterile syringe filter in a laminar flow hood using sterilized tubing and a collection bottle. The sterile filtered product was stored at −80° C.

In some embodiments of the inventive concept methods are provided for recovery of alpha-1-proteinase inhibitor from blood products. In such a method the starting material can be a non-salted, non-precipitated plasma (as described above), which can include Source Plasma, fresh frozen plasma, Recovered Plasma, or salvaged plasma. A salt is to the blood product at to produce a first intermediate, where sufficient salt is added so that the salt comprises between 11% to 13 wt % of the first intermediate. This first intermediate is separated to produce a first supernatant and a first paste. A salt is added to the first supernatant to produce a second intermediate, where sufficient salt is added so that salt comprises between 21% to 23 wt % of the second intermediate. This second intermediate is separated to produce a second supernatant and a second paste. The second paste is dissolved to produce a dissolved second paste, and a third intermediate is separated from this dissolved second paste by affinity chromatography using an alpha-1-proteinase inhibitor specific affinity resin. The third intermediate is in turn treated by ion exchange chromatography to produce an eluate that contains alpha-1-proteinase inhibitor. Suitable non-salted, non-precipitated plasmas include Source Plasma, fresh frozen plasma, Recovered Plasma, and salvaged plasma comprises Source Plasma. In some embodiments at least one of gamma globulin and albumin can also be isolated from a flow-through and/or a wash produced from a step of separating a third intermediate from the second supernatant by affinity chromatography.

Another embodiment of the inventive concept is a method for obtaining gamma globulin. In such a method a non-salted, non-precipitated, previously frozen blood product (as described above) is treated by adding a salt to the blood product to produce a first intermediate, where sufficient salt is added so that the salt comprises between 11% to 13 wt % of the first intermediate. This first intermediate is separated to produce a first supernatant and a first paste; A salt is added to the first supernatant to produce a second intermediate, where sufficient salt is added so that the salt comprises between 21% to 23 wt % of the second intermediate. This second intermediate is separated to produce a second supernatant and a second paste. A third intermediate is generated from the second supernatant by affinity chromatography using a gamma globulin specific affinity resin. This third intermediate is then treated by ion exchange chromatography to produce an eluate containing gamma globulin. Suitable non-salted, non-precipitated, previously frozen blood products include Source Plasma, fresh frozen plasma, Recovered Plasma, and salvaged plasma. Some embodiments include a step of isolating gamma globulin from the second paste.

The numbers expressing quantities of ingredients, properties such as concentration, reaction conditions, and so forth, used to describe and claim certain embodiments of the invention are to be understood as being modified in some instances by the term "about." Accordingly the numerical parameters set forth in the written description and attached claims are approximations that can vary depending upon the desired properties sought to be obtained by a particular embodiment. The numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The discussion herein provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

What is claimed is:

1. A method of producing a protein product from a blood plasma containing product, the method comprising:
   thawing a frozen blood plasma product followed by stirring at a temperature suitable for dissolving a cryoprecipitate to generate the blood plasma containing product;
   adding a salt to the blood plasma containing product to produce a first intermediate, wherein the salt comprises between 11-20 wt % of the first intermediate;
   separating the first intermediate to produce a first supernatant and a first paste;
   adding a salt to the first supernatant to produce a second intermediate, wherein the salt comprises between 15-30 wt % of the second intermediate;
   separating the second intermediate to produce a second supernatant and a second paste;
   separating a third intermediate from the second supernatant by affinity chromatography; and
   separating the third intermediate by ion exchange chromatography to produce an eluate containing the protein product.

2. The method of claim 1, wherein the step of adding the salt to the blood plasma containing product comprises adding an amount of a first salt selected from the group consisting of a citrate, an acetate, and a gluconate.

3. The method of claim 1, wherein the step of separating the first intermediate to produce a first supernatant and a first paste comprises a step of centrifuging the first intermediate.

4. The method of claim 1, wherein the step of separating the first intermediate to produce a first supernatant and a first paste comprises a step of filtering the first intermediate.

5. The method of claim 1, further comprising inactivating enveloped viruses in the second supernatant prior to the step of separating a third intermediate from the second supernatant by affinity chromatography.

6. The method of claim 5, wherein the step of inactivating enveloped viruses in the second supernatant comprises treating the second supernatant with a solvent and a detergent in amounts sufficient to inactivate said enveloped viruses.

7. The method of claim 1, further comprising desalting the second supernatant prior to the step of separating a third intermediate from the second supernatant by affinity chromatography.

8. The method of claim 7, wherein the step of desalting the second supernatant comprises filtering the second supernatant using an ultrafiltration membrane.

9. The method of claim 1, further comprising sterile filtering the eluate.

10. The method of claim 1, wherein the protein product comprises at least one of alpha-1-proteinase inhibitor, gamma globulin, immunoglobulin, albumin, factor VIII, factor IX, factor XIII, protein C, antithrombin III, fibrinogen, and C1 esterase inhibitor.

11. The method of claim 1, further comprising isolating a second protein product from at least one of the first paste and the second paste.

12. The method of claim 1, further comprising isolating a second protein product from at least one of a flow-through and a wash produced pursuant to the step of separating a third intermediate from the second supernatant by affinity chromatography.

13. The method as in claim 11 or claim 12, wherein the second protein product is different from the protein product and comprises at least one of alpha-1-proteinase inhibitor, gamma globulin, immunoglobulin, albumin, factor VIII, factor IX, factor XIII, protein C, antithrombin III, fibrinogen, and C1 esterase inhibitor.

14. A method of extracting alpha-1-proteinase inhibitor from blood comprising:
   obtaining a non-salted, non-precipitated plasma by thawing a frozen plasma and stirring at a temperature suitable for dissolving a cryoprecipitate, wherein the frozen Source Plasma comprises at least one of Source Plasma, fresh frozen plasma, Recovered Plasma, and salvaged plasma;
   adding a salt to the non-salted, non-precipitated plasma to produce a first intermediate, wherein the salt comprises between 11-13 wt % of the first intermediate;
   separating the first intermediate to produce a first supernatant and a first paste;
   adding a salt to the first supernatant to produce a second intermediate, wherein the salt comprises between 21-23 wt % of the second intermediate;
   separating the second intermediate to produce a second supernatant and a second paste;
   dissolving the second paste to produce a dissolved second paste;
   separating a third intermediate from the dissolved second paste by affinity chromatography using an alpha-1-proteinase inhibitor specific affinity resin; and
   separating the third intermediate by ion exchange chromatography to produce an eluate containing alpha-1-proteinase inhibitor.

15. The method of claim 14, wherein the frozen plasma comprises Source Plasma.

16. The method of claim 14, wherein the frozen plasma comprises fresh frozen plasma.

17. The method of claim 14, further comprising isolating at least one of gamma globulin and albumin from at least one of a flow-through and a wash produced pursuant to the step of separating a third intermediate from the second paste by affinity chromatography.

18. A method of isolating gamma globulin from blood comprising:
   obtaining a non-salted, non-precipitated, previously frozen blood product by thawing a previously frozen blood product and stirring at a temperature suitable for dissolving a cryoprecipitate;
   adding a salt to the blood product to produce a first intermediate, wherein the salt comprises between 11-13 wt % of the first intermediate;
   separating the first intermediate to produce a first supernatant and a first paste;
   adding a salt to the first supernatant to produce a second intermediate, wherein the salt comprises between 21-23 wt % of the second intermediate;
   separating the second intermediate to produce a second supernatant and a second paste;

separating a third intermediate from the second supernatant by affinity chromatography using a gamma globulin specific affinity resin; and separating the third intermediate by ion exchange chromatography to produce an eluate containing gamma globulin.

19. The method of claim 18, wherein the previously frozen blood product comprises at least one of Source Plasma, fresh frozen plasma, Recovered Plasma, and salvaged plasma.

20. The method of claim 18, further comprising isolating gamma globulin from the second paste.

21. A method of producing a second supernatant from blood plasma, the method comprising:

thawing a previously frozen blood product and stirring at a temperature suitable for dissolving a cryoprecipitate to generate a blood plasma;

adding a salt to the blood plasma so obtained to produce a first intermediate, wherein the salt comprises between 11-20 wt % of the first intermediate;

separating the first intermediate to produce a first supernatant and a first paste;

adding a salt to the first supernatant to produce a second intermediate, wherein the salt comprises between 15-30 wt % of the second intermediate; and separating the second intermediate to produce the second supernatant and a second paste.

22. The method of one of claims 1, 14, 18, and 21, wherein the temperature suitable for dissolving the cryoprecipitate is 20° C.

* * * * *